(12) United States Patent
Salter et al.

(10) Patent No.: US 10,906,074 B1
(45) Date of Patent: Feb. 2, 2021

(54) VEHICLE STORAGE COMPARTMENT

(71) Applicant: Ford Global Technologies, LLC, Dearborn, MI (US)

(72) Inventors: Stuart C. Salter, White Lake, MI (US); Daniel J. Martin, Plymouth, MI (US); Shannon Carloni, Dearborn Heights, MI (US); Michael Steven Medoro, Sunnyvale, CA (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/592,325

(22) Filed: Oct. 3, 2019

(51) Int. Cl.
| B08B 7/00 | (2006.01) |
| A61L 2/10 | (2006.01) |
| B60R 7/06 | (2006.01) |
| B60Q 1/00 | (2006.01) |
| B60R 11/02 | (2006.01) |

(52) U.S. Cl.
CPC .............. *B08B 7/0057* (2013.01); *A61L 2/10* (2013.01); *B60Q 1/0005* (2013.01); *B60Q 1/0017* (2013.01); *B60R 7/06* (2013.01); *A61L 2202/122* (2013.01); *A61L 2202/16* (2013.01); *B60R 11/0252* (2013.01)

(58) Field of Classification Search
CPC ... A61L 2/10; A61L 2202/122; B08B 7/0057; B60Q 1/0005; B60Q 1/0017; B60R 7/06
USPC ........................................................ 362/488
See application file for complete search history.

(56) References Cited

U.S. PATENT DOCUMENTS

| 6,490,351 | B1 | 12/2002 | Roberts |
| 8,481,970 | B2 | 7/2013 | Cooper et al. |
| 9,583,968 | B2 | 2/2017 | Salter et al. |
| 2006/0188389 | A1 | 8/2006 | Levy |
| 2018/0229694 | A1 | 8/2018 | Salter et al. |

FOREIGN PATENT DOCUMENTS

| CN | 2685145 | 3/2005 |
| CN | 201418882 | 3/2009 |
| CN | 202207330 | 5/2012 |
| CN | 202207332 | 5/2012 |
| CN | 103227490 | 7/2013 |
| CN | 203425270 | 2/2014 |
| WO | 2006022466 A1 | 3/2006 |

*Primary Examiner* — Jason M Han
(74) *Attorney, Agent, or Firm* — David Coppiellie; Price Heneveld LLP

(57) ABSTRACT

A storage compartment for a vehicle includes a body defining a cavity configured to receive an electronic device. The body includes an upper wall, a lower wall, and a rear wall. A door is hingedly coupled with the body and is configured to selectively seal the cavity. A shelf is removably positioned within the cavity. The shelf is configured to operably couple with the rear wall of the body. A lighting assembly is positioned proximate the rear wall. The lighting assembly includes a light guide and a light source positioned to direct emitted light through the light guide. A charging assembly is positioned proximate the lower wall of the body and is configured to charge the electronic device.

18 Claims, 7 Drawing Sheets

VEHICLE STORAGE COMPARTMENT

FIELD OF THE DISCLOSURE

The present disclosure generally relates to a storage compartment for a vehicle, and more specifically to a storage compartment within a vehicle center stack.

BACKGROUND OF THE DISCLOSURE

Vehicle consoles typically include a center stack and a center console. The center stack and the center console include various storage compartments.

SUMMARY OF THE DISCLOSURE

According to one aspect of the present disclosure, a storage compartment for a vehicle includes a body defining a cavity configured to receive an electronic device. The body includes an upper wall, a lower wall, and a rear wall. A door is hingedly coupled with the body and is configured to selectively seal the cavity. A shelf is removably positioned within the cavity. The shelf is configured to operably couple with the rear wall of the body. A lighting assembly is positioned proximate the rear wall. The lighting assembly includes a light guide and a light source positioned to direct emitted light through the light guide. A charging assembly is positioned proximate the lower wall of the body and is configured to charge the electronic device.

Embodiments of this aspect of the disclosure can include any one or a combination of the following features:
- a light guide integrally formed with the body;
- a shelf formed as a secondary light guide and configured to direct emitted light from a light source;
- a first coating applied to an upper wall, a lower wall, and a rear wall, wherein the first coating is configured to absorb the emitted light from the light source and convert the emitted light to converted light to illuminate the cavity;
- a door light guide positioned on an inner surface of a door, wherein the door light guide is configured to abut a light guide of a body;
- a second coating applied to an inner surface of a light guide, wherein the second coating includes a photoactive self-cleaning material configured to be activated by emitted light; and/or
- a second coating applied to a surface of an electronic device.

According to another aspect of the present disclosure, a storage compartment, includes a body defining a cavity. The body includes a rear wall defining an opening in communication with the cavity. A shelf is configured to be at least partially received by the opening of the rear wall. A hinged member is positioned to selectively conceal the opening of the rear wall. At least one light source is positioned proximate the opening of the rear wall. The shelf is configured to direct emitted light from the at least one light source into the cavity when the shelf is received by the opening of the rear wall.

Embodiments of this aspect of the disclosure can include any one or a combination of the following features:
- a first coating applied to an inner surface of a body and configured to absorb emitted light from a light source and convert the emitted light to converted light to illuminate a cavity;
- at least one light source includes a first light source positioned proximate a second light source, wherein one of the first and second light sources is an ultraviolet light-emitting diode;
- a charging assembly positioned proximate a lower wall of a body;
- a plurality of light guides includes an upper light guide, a lower light guide, and a rear light guide, wherein the plurality of light guides are configured to direct emitted light from a light source into a cavity;
- a rear light guide has an upper portion and a lower portion positioned to frame an opening of the rear wall; and/or
- a hinged member includes a protrusion having first and second sides, wherein the first and second sides are mirrored to direct emitted light from a light source to upper and lower portions of a rear light guide when the hinged member is in a closed position.

According to another aspect of the present disclosure, a storage compartment includes a body defining a cavity. The body includes an upper wall, a lower wall, and a rear wall. A light source is positioned proximate the rear wall. The body is configured to direct emitted light from the light source into the cavity. A charging assembly is positioned proximate the lower wall of the body. The charging assembly is configured to inductively charge an electronic device positioned within the cavity.

Embodiments of this aspect of the disclosure can include any one or a combination of the following features:
- a first coating applied to an inner surface of a body, wherein the first coating includes a photoluminescent material configured to absorb emitted light from a light source and convert the emitted light to converted light to illuminate a cavity;
- a second coating applied to an electronic device and an inner surface of a body, wherein the second coating includes a photoactive self-cleaning material activated by emitted light from a light source;
- a shelf removably positioned within a cavity and operably coupled with a body;
- a controller configured to selectively actuate a charging assembly and a light source;
- an actuator configured to provide user input to a controller to activate at least one of a charging assembly and a light assembly; and/or
- an actuator integrally formed with a display.

These and other aspects, objects, and features of the present disclosure will be understood and appreciated by those skilled in the art upon studying the following specification, claims, and appended drawings.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION OF THE PREFERRED EMBODIMENTS

Figure 1:
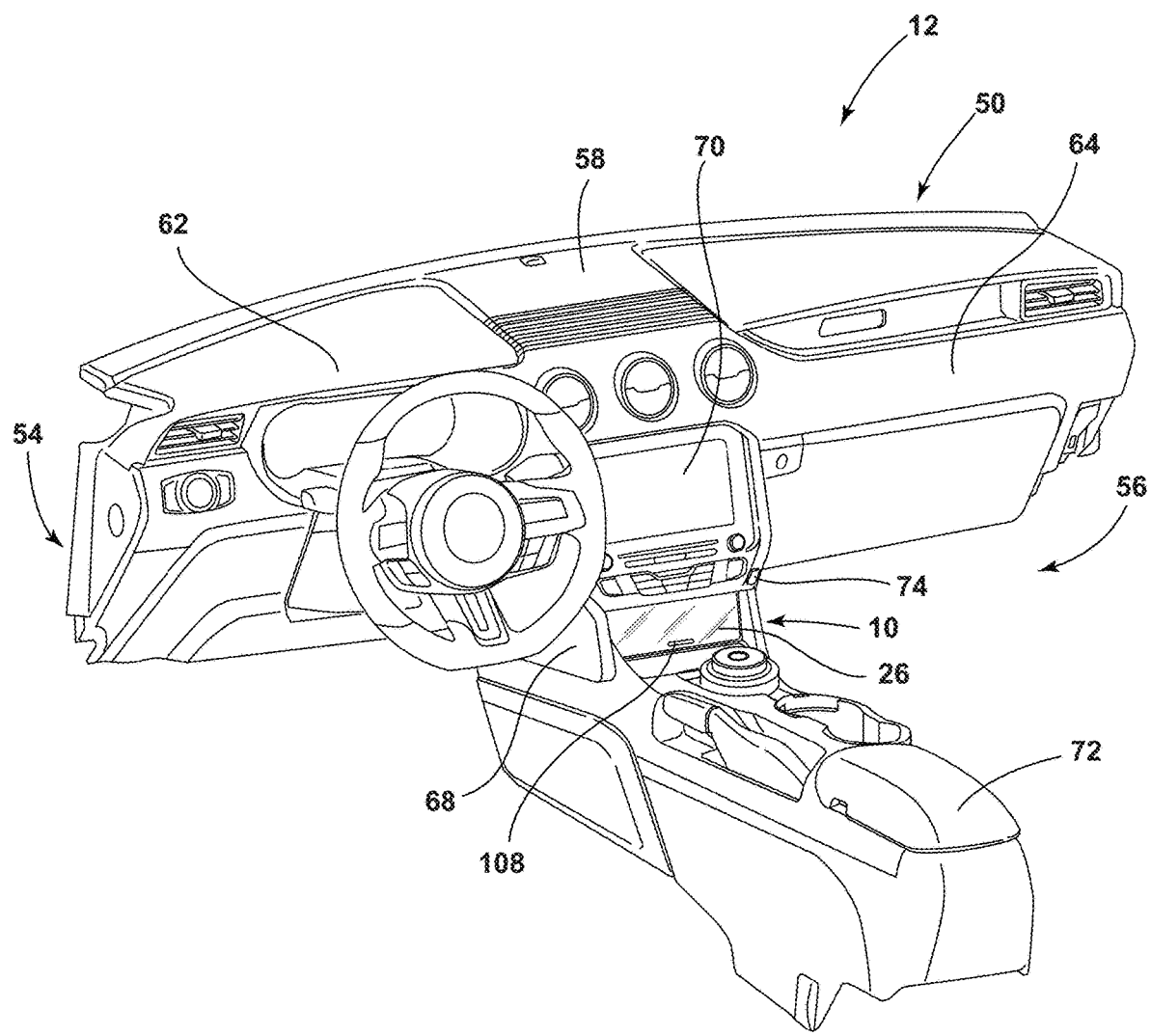
FIG. 1 is a side perspective view of a vehicle interior including a center stack portion and a center console, according to various examples.

The present illustrated embodiments reside primarily in combinations of method steps and apparatus components related to a charging and disinfecting/cleaning storage compartment. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to the surface of the element closer to an intended viewer, and the term "rear" shall refer to the surface of the element further from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a . . . " does not, without more constraints, preclude the existence of additional identical elements in the process, method, article, or apparatus that comprises the element.

Referring to FIGS. 1-8, reference numeral 10 generally designates a storage compartment for a vehicle 12. The storage compartment 10 includes a body 14 defining a cavity 16. The cavity 16 is configured to receive an electronic device 18. The body 14 includes an upper wall 20, a lower wall 22, and a rear wall 24. A door 26 is hingedly coupled with the body 14 and is configured to selectively seal the cavity 16. A shelf 28 is removably positioned within the cavity 16. The shelf 28 is configured to operably couple with the rear wall 24 of the body 14. A lighting assembly 30 is positioned proximate the rear wall 24 of the body 14. The lighting assembly 30 includes a light guide 32 extending along the upper wall 20, the lower wall 22, and the rear wall 24 of the body 14. A light source 34a, 34b is positioned to direct emitted light 36a, 36b through the light guide 32. A charging assembly 80 is positioned proximate the lower wall 22 of the body 14 and is configured to charge the electronic device 18.

Figure 2:
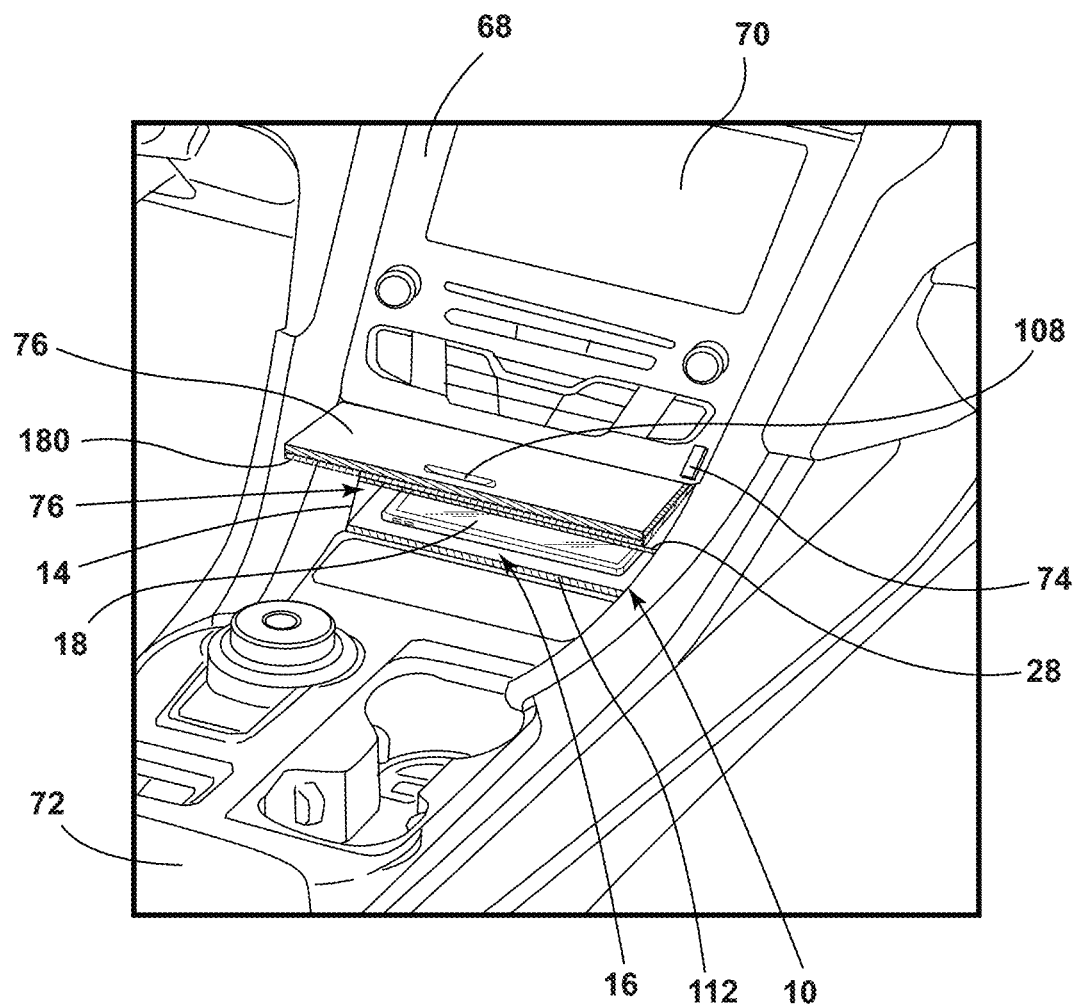
FIG. 2 is an enlarged side perspective view of a center stack portion and a center console of a vehicle, according to various examples.

Referring now to FIGS. 1 and 2, a vehicle interior 50 is generally illustrated including a driver's side 54 and a passenger's side 56. An instrument panel 58 spans laterally across the front of the vehicle interior 50. The instrument panel 58 may be divided into a driver's side portion 62, a passenger's side portion 64, and a center stack portion 68. Each of these portions 62, 64, 68 may serve different functions and include various electrical and mechanical components. A display 70 may be positioned on the center stack portion 68, as discussed in more detail elsewhere herein. A center console 72 may be coupled to the center stack portion 68. The center console 72 extends vehicle rearward from the center stack portion 68 and is positioned between the driver side 54 and the passenger side 56.

The center stack portion 68 and/or the center console 72 include a storage compartment 10 having an open end 76. The storage compartment 10 may include at least one shelf 28 removably positioned within the cavity 16 of the storage compartment 10, as introduced above. Alternatively, the storage compartment 10 may have any number of shelves 28 positioned within the cavity 16. In various examples, the storage compartment 10 may be positioned to be accessible through the open end 76 by an occupant positioned in either the driver side portion 62 or the passenger side portion 64 of the vehicle interior 50.

An actuator 74 may be positioned proximate the storage compartment 10. The actuator 74 is operably coupled with an operating system 40 and may be configured to actuate one or more of the functions of the storage compartment 10 controlled by the operating system 40, as discussed elsewhere herein. For example, the storage compartment 10 may include a charging assembly 80 and may be configured to wirelessly charge an electronic device 18 positioned within the storage compartment 10. The storage compartment 10 may further be configured to disinfect and/or clean the electronic device 18, as discussed elsewhere herein. Other items (e.g., pacifiers, pens, keys, etc.) may be positioned within the storage compartment 10 to be disinfected and/or cleaned. The door 26 is positioned to selectively close the storage compartment 10 to seal the storage compartment 10 when the storage compartment 10 is in use (e.g., an electronic device 18 is being charged, disinfected, and/or cleaned) or to conceal the storage compartment 10 when the storage compartment 10 is not in use.

Figure 3:
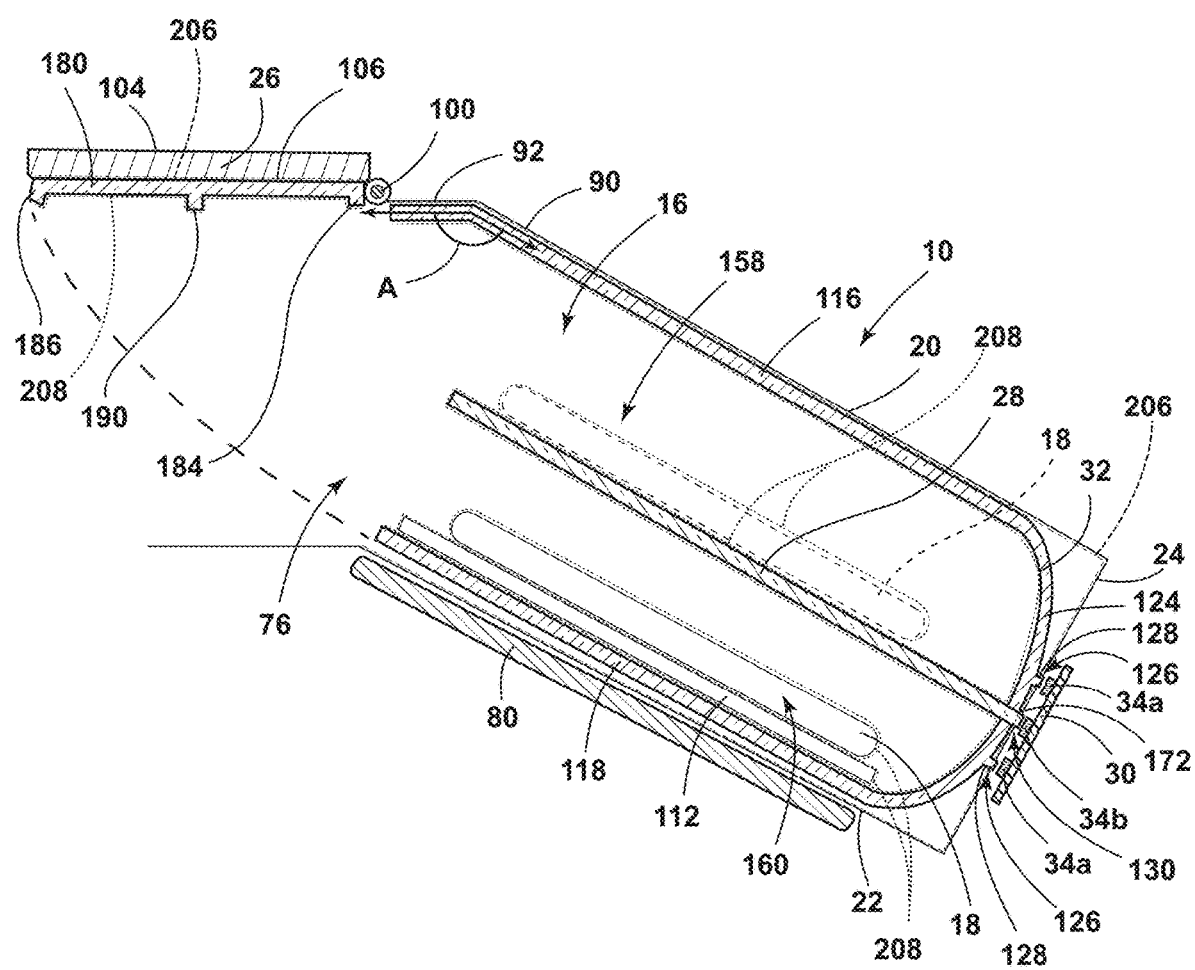
FIG. 3 is a schematic cross-sectional view of a storage compartment for a vehicle with a door in an open position, according to various examples.
Figure 4:
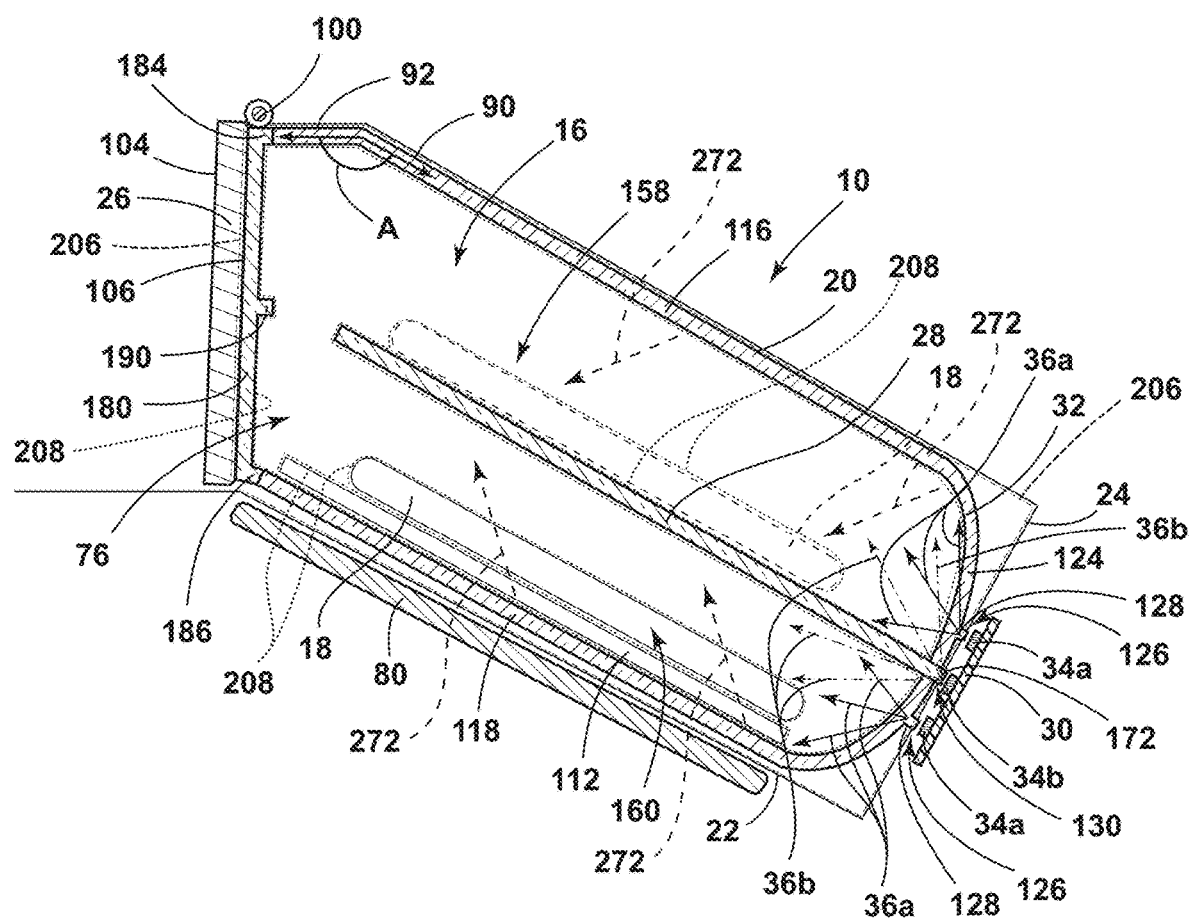
FIG. 4 is a schematic cross-sectional view of a storage compartment for a vehicle with a door in an closed position, according to various examples.

Referring now to FIGS. 1-4, as introduced, the storage compartment 10 includes the body 14 operably coupled with the center stack portion 68 at the open end 76. FIGS. 3 and 4 illustrate the body 14 including the upper wall 20 spaced apart from the lower wall 22 by first and second sidewalls 84, 86. The rear wall 24 is coupled with the upper wall 20, the lower wall 22, and the first and second sidewalls 84, 86 to define the cavity 16 in communication with the open end 76 of the storage compartment 10. In various examples, the rear wall 24 extends linearly between the upper wall 20 and the lower wall 22. In other examples, the rear wall 24 may be generally arcuate.

The upper wall 20 may have a first portion 90 positioned parallel to the lower wall 22 and a second portion 92 extending forward of the first portion 90. The first and second portions 90, 92 of the upper wall 20 may be integrally formed as a single piece or may be operably coupled together. The second portion 92 may be positioned to extend outward of the open end 76 of the storage compartment 10 or may be positioned to be rearward of the open end 76. The second portion 92 is positioned at an angle A relative to the first portion 90. The angle A is generally obtuse and is selected to position the door 26 to cover the open end 76 of the storage compartment 10 when the door 26 is closed.

As illustrated in FIG. 1-4, the door 26 may be hingedly coupled with the second portion 92 of the upper wall 20 by a horizontally positioned hinge 100. However, it is contemplated that the door 26 may be coupled with any portion of the body 14 by any type of hinge without departing from the scope of the present disclosure. When the door 26 is open (FIGS. 2 and 3), the door 26 may be substantially coplanar with the second portion 92 of the upper wall 20. When the door 26 is closed (FIGS. 1 and 4), the door 26 may be substantially perpendicular to the second portion 92 and may be configured to cover the open end 76 of the storage compartment 10. The door 26 may include an outer surface 104 and an inner surface 106. The outer surface 104 may be formed of a material similar to materials used for the center stack portion 68 and/or center console 72. The material selected for the outer surface 104 may be selected to achieve a continuous aesthetic. Alternatively, the outer surface 104 of the door 26 may be formed of a different material than the material used for the center stack portion 68 and/or center console 72. A handle 108 may be positioned on the outer surface 104 of the door 26. The door 26 may include any closing and/or latching mechanism configured to maintain the door 26 in an open position or a closed position without departing from the scope of the present disclosure. When the door 26 is closed, the door 26 may be configured to seal the storage compartment 10 and prevent leaking of light from the storage compartment 10, as discussed elsewhere herein.

In various examples, a tray 112 may be positioned within the cavity 16 of the storage compartment 10. The tray 112 may be fixedly positioned within the cavity 16 of the storage compartment 10 or may be removable from the cavity 16 of the storage compartment 10. The tray 112 may be formed of a polymeric material or any other material and may be configured to support and/or align the electronic device 18 within the storage compartment 10. Alternatively, the storage compartment 10 may be formed to include only the lower wall 22 without including the tray 112.

A charging assembly 80 is positioned proximate the lower wall 22 of the body 14 of the storage compartment 10. In various examples, the charging assembly 80 may be at least partially positioned within the tray 112, as discussed previously. Alternatively, the charging assembly 80 may be coupled with the lower wall 22 of the body 14. The charging assembly 80 may be operably coupled with the operating system 40 of the storage compartment 10, as discussed in more detail below.

The charging assembly 80 includes a charger configured to wirelessly charge one or more devices, including one or more rechargeable batteries for providing electrical power within the electronic device 18. The charging assembly 80 is configured to provide electrical energy to the electronic device 18 when the electronic device 18 is positioned within the cavity 16 and proximate the lower wall 22 of the body 14 of the storage compartment 10. In various examples, the charging assembly 80 may be an inductive charger system. In other examples, the charging assembly 80 may be any other charging system using a wireless transmission such as magnetic resonance, loose coupled resonance, and electromagnetic radiation.

As illustrated in FIGS. 3-7, a plurality of light guides 32 may be positioned within the cavity 16 and may be operably coupled with the body 14. Each of the plurality of light guides 32 may be formed of silicone and may be positioned along the entirety or along part of one of the walls 20, 22, 24, 84, 86 of the body 14. The plurality of light guides 32 may be integrally formed so that emitted light 36a, 36b from the light source 34a, 34b of the lighting assembly 30 is directed through any one of the plurality of light guides 32 to the entire plurality of light guides 32. The plurality of light guides 32 is configured to direct and provide a substantially even distribution of the emitted light 36a, 36b into the cavity 16. In various examples, each of the plurality of light guides 32 may include optics configured to direct the emitted light 36a, 36b as described. The plurality of light guides 32 may be positioned and shaped to complement the shape of the walls 20, 22, 24, 84, 86 or may have a shape that varies from the shape of the walls 20, 22, 24, 84, 86. Alternatively, the plurality of light guides 32 may be integrally formed with the walls 20, 22, 24, 84, 86 of the body 14 such that one or more of the walls 20, 22, 24, 84, 86 is configured to operate as one of the plurality of light guides 32.

The plurality of light guides 32 includes at least an upper light guide 116 positioned along the upper wall 20 of the body 14 and a lower light guide 118 positioned along the lower wall 22 of the body 14. The plurality of light guides 32 may also include a rear light guide 124 extending along the rear wall 24 of the body 14 and coupling the upper and lower light guides 116, 118. Further, first and second side light guides 120, 122 may be aligned with the first and second sidewalls 84, 86 and may extend forward from the rear light guide 124. In various examples, the first and second side light guides 120, 122 may be coupled with the upper and lower light guides 116, 118. In other examples, the first and second side light guides 120, 122 may be separate from the upper and lower light guides 116, 118. As illustrated in FIGS. 3 and 4, the rear light guide 124 may be generally arcuate. Alternatively, the rear light guide 124 may extend linearly along the rear wall 24 of the body 14. Further, as illustrated in FIG. 5, the first and second side light guides 120, 122 may be generally arcuate or may be generally linear.

As illustrated in FIGS. 3 and 4, in various examples, the rear wall 24 may define one or more apertures 126. The rear light guide 124 may include one or more extensions 128 configured to be received by the apertures 126. The lighting assembly 30 is positioned rearward of the rear wall 24 and includes at least one light source 34a, 34b. It will be understood that the at least one light source 34a, 34b may be one of a plurality of light sources 34a, 34b. Each of the plurality of light sources 34a, 34b may be any light source including, but not limited to, halogen lighting, fluorescent lighting, light-emitting diodes (LEDs), organic LEDs (OLEDs), or polymer LEDs (PLEDs). The plurality of light sources 34a, 34b are aligned with the apertures 126 and direct light into the rear light guide 124 through the extension 128. The rear light guide 124 may further define an opening 130 configured to align with one or more of the plurality of light sources 34a, 34b. The opening 130 is configured to receive the removable shelf 28 which may be configured to act as a light guide in conjunction with the plurality of light guides 32.

Figure 5:
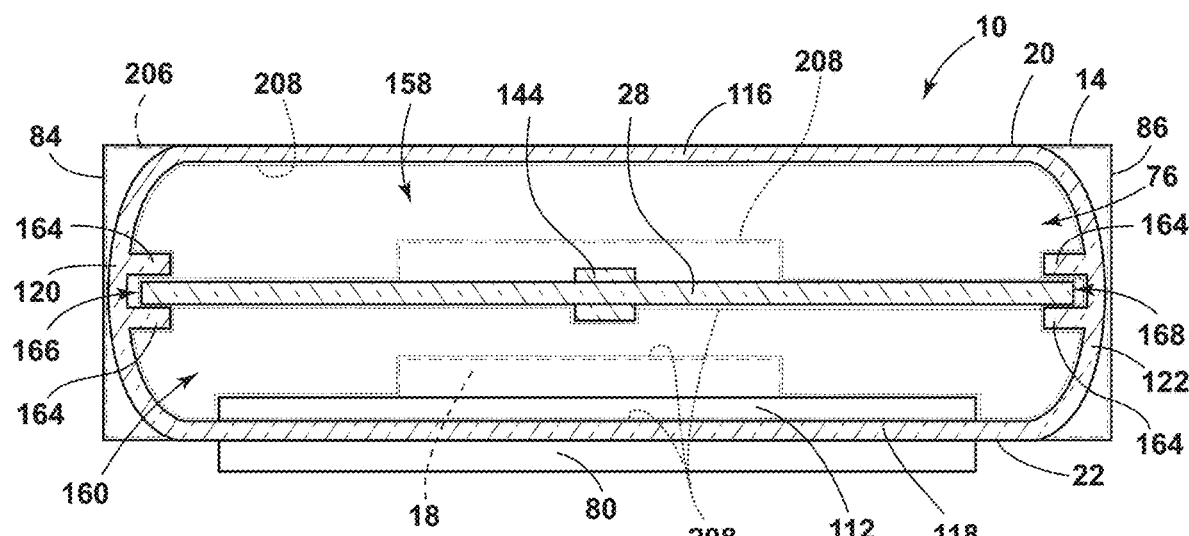
FIG. 5 is a front elevation schematic view of a storage compartment for a vehicle, according to various examples.
Figure 6:
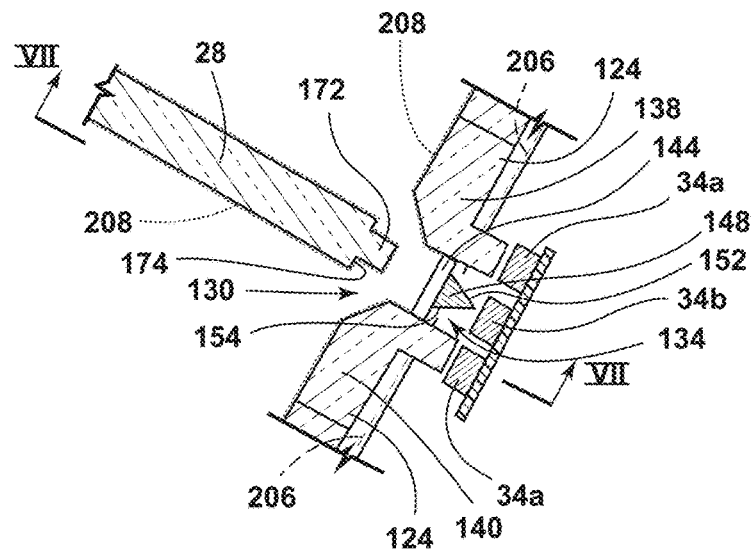
FIG. 6 is a schematic side profile view of a storage compartment for a vehicle with a shelf disengaged from a rear wall, according to various examples.
Figure 7:
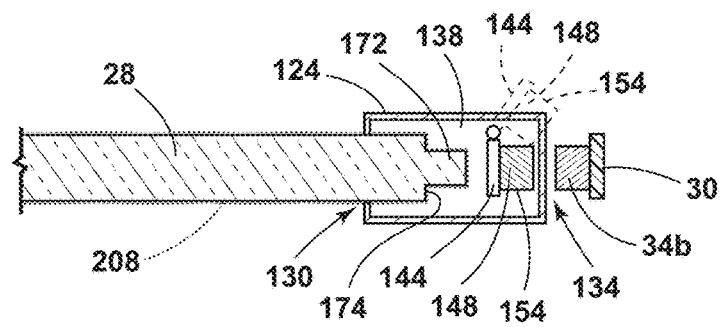
FIG. 7 is a cross-sectional view of the schematic of FIG. 6 with a hinged member in a closed position and shown in an open position in phantom.

As illustrated in FIGS. 5-7, in other examples, the opening 130 of the rear light guide 124 may be in communication with a space 134 framed by at least an upper portion 138 of the rear light guide 124 and a lower portion 140 of the rear light guide 124. The lighting assembly 30 is aligned with the opening 130 and configured to direct emitted light 36a, 36b into the space 134 and opening 130. In various examples, the lighting assembly 30 may be positioned rearward of the rear wall 24 of the body 14. In other examples, the lighting assembly 30 may be positioned at least partially within the space 134. In still other examples, the lighting assembly 30 may be positioned between the rear wall 24 and the rear light guide 124 and may include at least one light source 34a, 34b positioned proximate the opening 130.

As illustrated in FIGS. 6 and 7, a hinged member 144 may be operably coupled with one of the upper and lower portions 138, 140 of the rear light guide 124 and is positioned to selectively open and close the opening 130. The hinged member 144 includes a wedge-shaped protrusion 148. When the hinged member 144 is in a closed position, the hinged member 144 blocks the opening 130 and the wedge-shaped protrusion 148 extends into the space 134 defined by the rear light guide 124. The wedge-shaped protrusion 148 includes first and second sides 152, 154 positioned to form a vertex. The first and second sides 152, 154 may be formed of a reflective material or may be coated with a mirrored material. The first and second sides 152, 154 may be configured to direct the emitted light 36a, 36b from the plurality of light sources 34a, 34b of the lighting assembly 30 into the upper and lower portions 138, 140 of the rear light guide 124.

Referring now to FIGS. 3-7, the removable shelf 28 may be selectively positioned within the cavity 16 of the storage compartment 10. The removable shelf 28 is configured to divide the cavity 16 into an upper cavity 158 and a lower cavity 160. Like the plurality of light guides 32, the removable shelf 28 may be formed of silicone and is configured to act as a light guide in conjunction with the plurality of light guides 32. When the removable shelf 28 is positioned within the cavity 16, the removable shelf 28 is optically coupled with the plurality of light guides 32 and directs emitted light 36a, 36b from the plurality of light sources 34a, 34b of the lighting assembly 30 into the cavity 16. In various examples, the first and second side light guides 120, 122 of the plurality of light guides 32 may define first and second channels 166, 168 configured to receive lateral edges of the removable shelf 28. In other examples, each of the first and second sidewalls 84, 86 of the body 14 may define the first and second channels 166, 168. In still other examples, each of the first and second side light guides 120, 122 may include rails 164 aligned to define the first and second channels 166, 168 to receive the removable shelf 28. Alternatively, each of the first and second sidewalls 84, 86 of the body 14 may include the rails 164. The first and second channels 166, 168 are defined to guide the removable shelf 28 into engagement with the plurality of light guides 32 within the cavity 16 of the storage compartment 10.

Referring now to FIGS. 6 and 7, the removable shelf 28 may include an actuating portion 172. The actuating portion 172 may extend from a rear edge 174 of the removable shelf 28 and is sized to be received by the opening 130 of the rear light guide 124. In various examples, the actuating portion 172 extends along the entirety of the rear edge 174 of the removable shelf 28. In other examples, the actuating portion 172 may be positioned along only a portion of the rear edge 174 of the removable shelf 28. When the removable shelf 28 is inserted into the cavity 16 and received by the first and second channels 166, 168, the actuating portion 172 is aligned with the opening 130 of the rear light guide 124. Where the hinged member 144 is positioned to conceal the opening 130, the actuating portion 172 presses against the hinged member 144 as the removable shelf 28 is inserted into the cavity 16 and moves the hinged member 144 from the closed position to an open position. When the removable shelf 28 is positioned within the cavity 16 and the hinged member 144 is in the open position, first and second sides 152, 154 are moved and the lighting assembly 30 is positioned so that the plurality of light sources 34a, 34b illuminate through the removable shelf 28 and through the rear light guide 124.

Referring again to FIGS. 3 and 4, a door light guide 180 may be coupled with the inner surface 106 of the door 26. Like the plurality of light guides 32, the door light guide 180 may be formed of silicone or any other material configured to direct the emitted light 36a, 36b from the plurality of light sources 34a, 34b. The door light guide 180 may include at least one protrusion 184, 186, 190 extending outward from the inner surface 106 of the door 26. For example, the door light guide 180 may include a first protrusion 184 and a second protrusion 186. The first and second protrusions 184, 186 may be positioned on opposite sides of the door light guide 180. When the door 26 is closed, the first protrusion 184 is configured to align with the upper light guide 116 and the second protrusion 186 is configured to align with the lower light guide 118. The first and second protrusions 184, 186 may be positioned to abut terminal ends of the upper and lower light guides 116, 118, respectively. The door light guide 180 may further include a central protrusion 190 positioned between the first protrusion 184 and the second protrusion 186. The central protrusion 190 is configured to align with the removable shelf 28 when the door 26 is closed. Like the first and second protrusions 184, 186, the central protrusion 190 may be positioned to abut an outer edge of the removable shelf 28. Each of the protrusions 184, 186, 190 may extend along part of, or the entirety of, the width of the door 26 and may extend any distance into the cavity 16 that allows the protrusion 184, 186, 190 to be in optical communication with the plurality of light guides 32.

Referring now to FIGS. 3-7, and as discussed previously, the lighting assembly 30 includes at least one light source 34a, 34b. The at least one light source 34a, 34b may be one of a plurality of light sources 34a, 34b. At least one of the light sources 34a is configured to emit ultraviolet (UV) light. However, it will be understood that any combination of light sources may be used. For example, the lighting assembly 30 may include a first light source 34a that is configured to emit a first emitted light 36a having a first wavelength and a second light source 34b that is configured to emit a second emitted light 36b having a second wavelength. For example, the first light source 34a may be an ultraviolet light emitting diode (UV LED) configured to produce emitted light 36a having a wavelength within the UV light range. The emitted light 36a within the UV light range is configured to disinfect an object (e.g, an electronic device 18, a pacifier, a pen, keys, etc.) positioned within the storage compartment 10 and/or actuate one or both of a first coating 206 and a second coating 208 applied to various features of the storage compartment 10, as discussed below. It will be understood than any or all of the plurality of light sources may be configured to produce emitted light within the UV light range upon actuation.

In some examples, the door 26 and the storage compartment 10 may be formed of polymeric materials, for example, polycarbonate or acrylic, which are configured to absorb and/or block ultraviolet radiation emitted by the lighting assembly 30. For example, the door 26 may be configured to prevent radiation from escaping from the storage compartment 10 into the vehicle interior 50 when the door 26 is closed and the UV light source 34a is actuated. The first coating 206 includes a photoluminescent structure 260 that has a photoluminescent material 274 (e.g., a long persistence phosphor) configured to absorb and/or convert the first emitted light 36a. In various examples, the first coating 206 may be applied to the door 26, the tray 112, and/or one or more of the walls 20, 22, 24, 84 86 of the body 14 of the storage compartment 10. In other examples, the first coating 206 may be added to material used to form the door 26, the tray 112, and/or one or more of the walls 20, 22, 24, 84, 86.

Figure 8A:
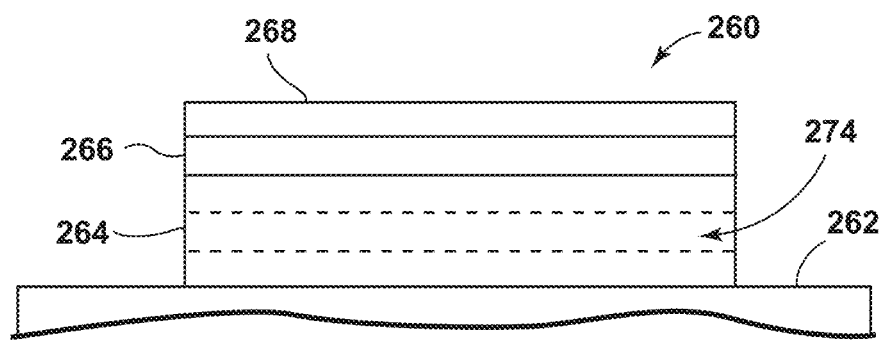
FIG. 8A is a side view of a photoluminescent structure rendered as a coating, according to various examples.
Figure 8B:
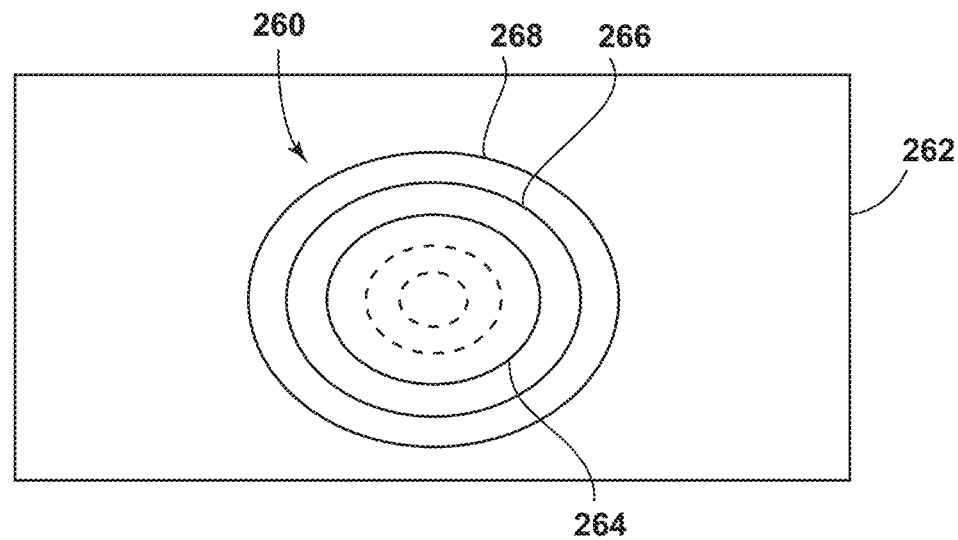
FIG. 8B is a top view of a photoluminescent structure rendered as a discrete particle, according to various examples.
Figure 8C:
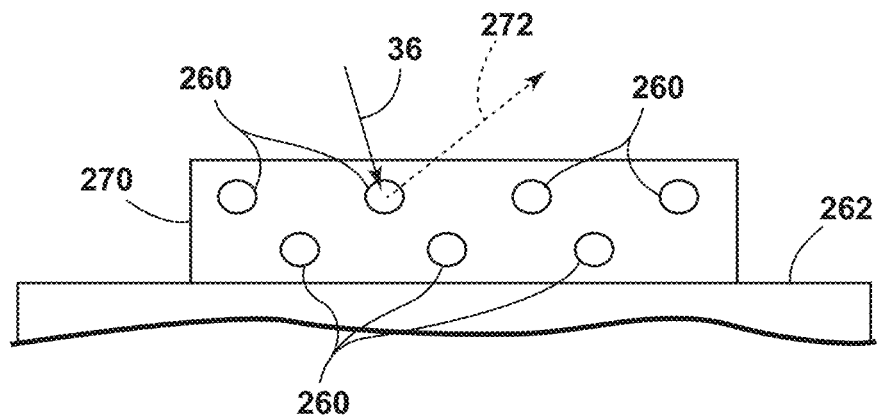
FIG. 8C is a side view of a plurality of photoluminescent structures rendered as discrete particles and incorporated into a separate structure, according to various examples.

Referring to FIGS. 8A-8C, various exemplary embodiments of photoluminescent structures 260 are shown, each capable of being coupled to a substrate 262, which may correspond to a vehicle fixture or vehicle-related piece of equipment such as, for example, a storage compartment 10 (see FIGS. 3-7). In FIG. 8A, the photoluminescent structure 260 is generally shown rendered as a coating (e.g., a film) that may be applied to a surface of the substrate 262. In FIG. 8B, the photoluminescent structure 260 is generally shown as a discrete particle capable of being integrated with a substrate 262. In FIG. 8C, the photoluminescent structure 260 is generally shown as a plurality of discrete particles that may be incorporated into a support medium 270 (e.g., a film) that may then be applied (as shown) or integrated with the substrate 262.

Referring now to FIGS. 3-8C, the first emitted light 36a emitted by the UV light source 34a of the plurality of light sources 34a, 34b of the lighting assembly 30 acts to excite the photoluminescent structure 260 and is illustrated herein as solid arrows. In contrast, light emitted from the photoluminescent structure 260 is referred to herein as converted light 272 and is illustrated herein as broken arrows. The mixture of emitted light 36a and converted light 272 that may be emitted simultaneously is referred to herein as outputted light. The first emitted light 36a and/or the converted light 272 may provide illumination within the cavity 18 to provide visual indication of a status of the storage compartment 10, as discussed elsewhere herein.

In various examples, given photoluminescent structure 260 includes an energy conversion layer 264 that may include one or more sublayers, which are exemplarily shown through broken lines in FIGS. 8A and 8B. Each sublayer of the energy conversion layer 264 may include one or more photoluminescent materials 274 having energy converting elements with phosphorescent or fluorescent properties. Each photoluminescent material 274 may become excited upon receiving the emitted light 36a of a specific wavelength from the one of the plurality of light sources 34a, 34b of the lighting assembly 30, thereby causing the light to undergo a conversion process known as a Stokes shift. Under the principle of down conversion, the emitted light 36a from the one of the plurality of light sources 34a, 34b of the lighting assembly 30 is converted into a longer wavelength, converted light 272 that is output from the photoluminescent structure 260. Conversely, under the principle of up conversion, the emitted light 36a is converted into a shorter wavelength light that is output from the photoluminescent structure 260. When multiple distinct wavelengths of light are output from the photoluminescent structure 260 at the same time, the wavelengths of light may mix together and be expressed as a multicolor light.

The energy conversion layer 264 may be prepared by dispersing the photoluminescent material 274 in a polymer matrix to form a homogenous mixture using a variety of methods. Such methods may include preparing the energy conversion layer 264 from a formulation in a liquid carrier support medium 270 and coating the energy conversion layer 264 to a desired substrate 262. The energy conversion layer 264 may be applied to a substrate 262 by painting, screen-printing, spraying, slot coating, dip coating, roller coating, and bar coating. Alternatively, the energy conversion layer 264 may be prepared by methods that do not use a liquid carrier support medium 270. For example, the energy conversion layer 264 may be rendered by dispersing the photoluminescent material 274 into a solid-state solution (homogenous mixture in a dry state) that may be incorporated in a polymer matrix, which may be formed by extrusion, injection molding, compression molding, calendaring, thermoforming, etc. The energy conversion layer 264 may then be integrated into a substrate 262 using any methods known to those skilled in the art. When the energy conversion layer 264 includes sublayers, each sublayer may be sequentially coated to form the energy conversion layer 264. Alternatively, the sublayers can be separately prepared and later laminated or embossed together to form the energy conversion layer 264. Alternatively still, the energy conversion layer 264 may be formed by coextruding the sublayers.

Referring back to FIGS. 8A and 8B, the photoluminescent structure 260 may optionally include at least one stability layer 266 to protect the photoluminescent material 274 contained within the energy conversion layer 264 from photolytic and thermal degradation. The stability layer 266 may be configured as a separate layer optically coupled and adhered to the energy conversion layer 264. Alternatively, the stability layer 266 may be integrated with the energy conversion layer 264. The photoluminescent structure 260 may also optionally include a protective layer 268 optically coupled and adhered to the stability layer 266 or other layer (e.g., the energy conversion layer 264 in the absence of the stability layer 266) to protect the photoluminescent structure 260 from physical and chemical damage arising from environmental exposure. The stability layer 266 and/or the protective layer 268 may be combined with the energy conversion layer 264 through sequential coating or printing of each layer, sequential lamination or embossing, or any other suitable means.

Additional information regarding the construction of photoluminescent structures 260 is disclosed in U.S. Pat. No. 8,232,533 to Kingsley et al., entitled "PHOTOLYTICALLY AND ENVIRONMENTALLY STABLE MULTILAYER STRUCTURE FOR HIGH EFFICIENCY ELECTROMAGNETIC ENERGY CONVERSION AND SUSTAINED SECONDARY EMISSION," the entire disclosure of which is incorporated herein by reference. For additional information regarding fabrication and utilization of photoluminescent materials to achieve various light emissions, refer to U.S. Pat. No. 8,207,511 to Bortz et al., entitled "PHOTOLUMINESCENT FIBERS, COMPOSITIONS AND FABRICS MADE THEREFROM"; U.S. Pat. No. 8,247,761 to Agrawal et al., entitled "PHOTOLUMINESCENT MARKINGS WITH FUNCTIONAL OVERLAYERS"; U.S. Pat. No. 8,519,359 B2 to Kingsley et al., entitled "PHOTOLYTICALLY AND ENVIRONMENTALLY STABLE MULTILAYER STRUCTURE FOR HIGH EFFICIENCY ELEC- TROMAGNETIC ENERGY CONVERSION AND SUSTAINED SECONDARY EMISSION"; U.S. Pat. No. 8,664,624 B2 to Kingsley et al., entitled "ILLUMINATION DELIVERY SYSTEM FOR GENERATING SUSTAINED SECONDARY EMISSION"; U.S. Patent Publication No. 2012/0183677 to Agrawal et al., entitled "PHOTOLUMINESCENT COMPOSITIONS, METHODS OF MANUFACTURE AND NOVEL USES"; U.S. Pat. No. 9,057,021 to Kingsley et al., entitled "PHOTOLUMINESCENT OBJECTS"; and U.S. Pat. No. 8,846,184 to Agrawal et al., entitled "CHROMIC LUMINESCENT OBJECTS," all of which are incorporated herein by reference in their entirety.

The photoluminescent material 274, according to one example, disposed within the photoluminescent structure 260 may include a long persistence photoluminescent material 274 that emits the converted light 272, once charged by the emitted light 36a from one of the plurality of light sources 34a (FIGS. 3-7). The long persistence photoluminescent material 274 may be defined as having a long decay time due to its ability to store the emitted, or excitation, light 36a and release the converted light 272 gradually, for a period of several minutes or hours, once the emitted light 36a is no longer present (e.g., the light source 34a is turned off).

The long persistence photoluminescent material 274, according to one embodiment, may be operable to emit light at or above an intensity of 0.32 mcd/m$^2$ after a period of 10 minutes. Additionally, the long persistence photoluminescent material 274 may be operable to emit light above or at an intensity of 0.32 mcd/m$^2$ after a period of 30 minutes and, in some embodiments, for a period substantially longer than 60 minutes (e.g., the period may extend 24 hours or longer, and in some instances, the period may extend 48 hours). Accordingly, the long persistence photoluminescent material 274 may continually illuminate in response to excitation from the emitted light 36a from one of the plurality of light sources 34a of the lighting assembly 30 (FIG. 4). The periodic absorption of the emitted light 36a from the one of the plurality of light sources 34a of the lighting assembly 30 may provide for a substantially sustained charge of the long persistence photoluminescent material 274 to provide for consistent passive illumination.

The photoluminescent structure 260, according to one embodiment, may be a translucent white color, and in some instances reflective, when unilluminated. Once the photoluminescent structure 260 receives the emitted light 36a, 36b of a particular wavelength, the photoluminescent structure 260 may emit any color light (e.g., blue or red) therefrom at any desired brightness. It will be understood that any phosphor known in the art may be utilized within the photoluminescent structure 260 without departing from the teachings provided herein. Moreover, it is contemplated that any long persistence phosphor known in the art may also be utilized without departing from the teachings provided herein.

Additional information regarding the production of long persistence photoluminescent materials is disclosed in U.S. Pat. No. 8,163,201 to Agrawal et al., entitled "HIGH-INTENSITY, PERSISTENT PHOTOLUMINESCENT FORMULATIONS AND OBJECTS, AND METHODS FOR CREATING THE SAME," the entire disclosure of which is incorporated herein by reference. For additional information regarding long persistence phosphorescent structures, refer to U.S. Pat. No. 6,953,536 to Yen et al., entitled "LONG PERSISTENT PHOSPHORS AND PERSISTENT ENERGY TRANSFER TECHNIQUE"; U.S. Pat. No. 6,117,362 to Yen et al., entitled "LONG-PERSISTENT BLUE PHOSPHORS"; and U.S. Pat. No. 8,952,341 to Kingsley et al., entitled "LOW RARE EARTH MINERAL PHOTOLUMINESCENT COMPOSITIONS AND STRUCTURES FOR GENERATING LONG-PERSISTENT LUMINESCENCE," all of which are incorporated herein by reference in their entirety.

Referring now to FIGS. 3-7, when the first coating 206 is applied to or incorporated with one or more of the walls 20, 22, 24, 84, 86 of the body 14, the first coating 206 emits the converted light 272 to provide illumination to the cavity 16. Any emitted light 36a that is not converted by the photoluminescent structure 260 of the first coating 206 may be absorbed and/or reflected back into the cavity 16. Even after the light source 34a is turned off, the photoluminescent structure 260 of the first coating 206 may continue to produce converted light 272. For example, after 20 minutes of exposure to the emitted light 36a from the light source 34a, the light level in the cavity 16 from the photoluminescent structure 260 may drop to an ambient lighting level and remain at this level for 12-24 hours.

Referring still to FIGS. 3-7, exposed inner surfaces of the plurality of light guides 32, including the shelf 28 and the door light guide 180, and/or the tray 112 that are exposed within the cavity 16 may be coated with the second coating 208. Where the plurality of light guides 32 is integrally formed with the walls 20, 22, 24, 84, 86 of the body 14, the second coating 208 may be applied directly to the inner surfaces of the body 14 in conjunction with the first coating 206. For example, the second coating 208 may be applied to the exposed inner surfaces of the plurality of light guides 32, the shelf 28, and the door light guide 180 by spraying post-fabrication. Alternatively, the second coating 208 may be incorporated into the materials used to fabricate the plurality of light guides 32, the shelf 28, the door light guide 180, the tray 112, or any other surface accessible within the cavity 16.

The second coating 208 is a disinfecting coating including a photoactive self-cleaning agent (e.g., titanium dioxide). The second coating 208 may be configured to allow light to pass through the second coating 208. For example, at least about 95% of light may pass through the second coating 208. When the emitted light 36a within the UV light range passes through the second coating 208, the emitted light 36a activates ions in the diode coating via a catalytic reaction. This begins a self-cleaning process for the surface that the second coating 208 is applied to.

Referring still to FIGS. 3-7, the electronic device 18 may be coated with the second coating 208. The second coating 208 allows the emitted light 36a to activate the titanium dioxide within the second coating 208 to clean the electronic device 18. When the electronic device 18 is within the storage compartment 10, the reaction between the emitted light 36a and second coating 208 cleans the electronic device 18 and the exposed surfaces of the storage compartment 10. The combination of the first and second coatings 206, 208 allows for the intensity of the converted light 272 produced by the first coating 206 to indicate the level of activation of the second coating 208 (e.g., a bright glow from the first coating 206 indicates more activation of the second coating 208 and/or a longer exposure time of the second coating 208 to the emitted light 36a).

Figure 9:
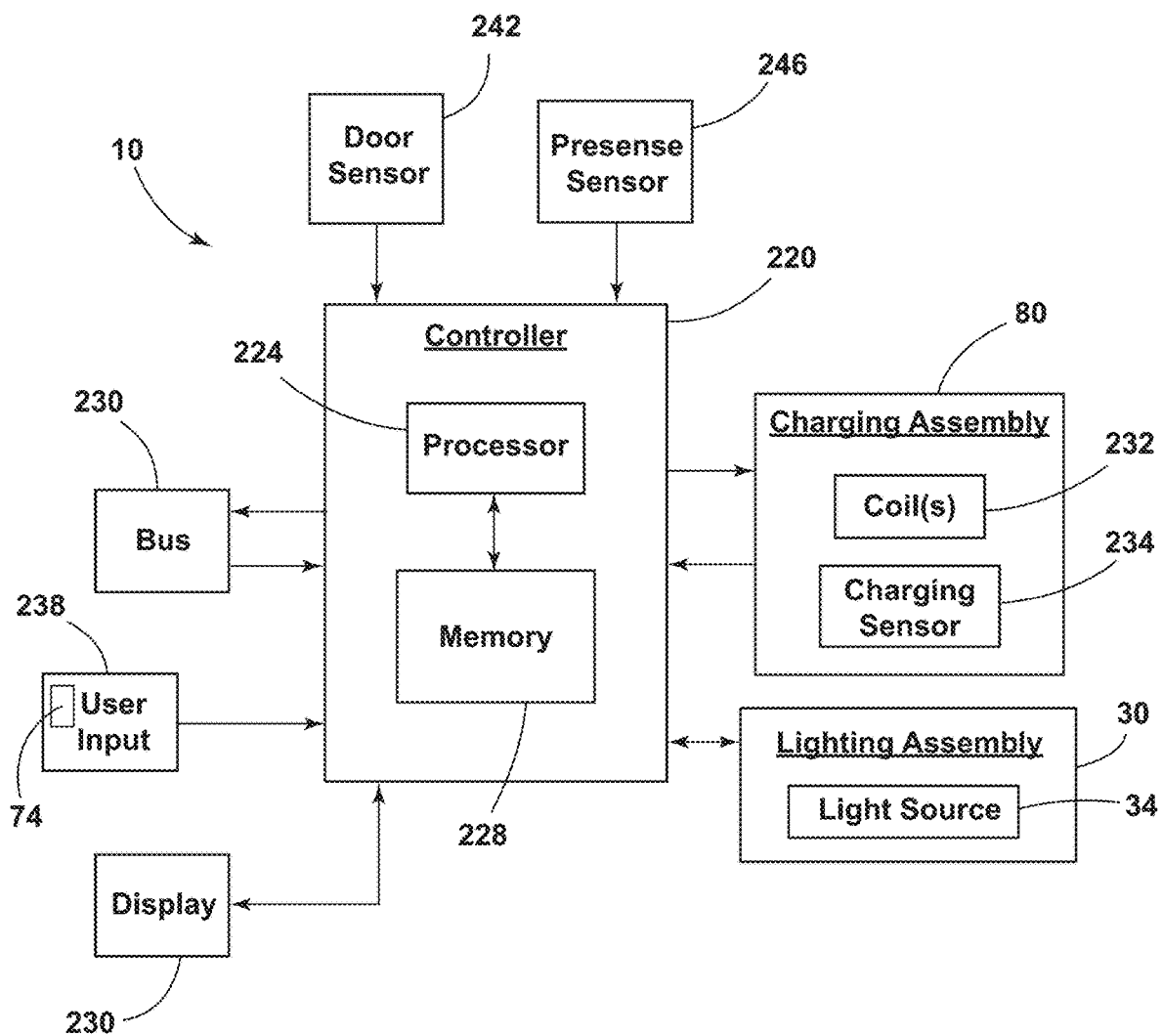
FIG. 9 is a block diagram of an operating system for a charging and disinfecting/cleaning storage compartment of a vehicle, according to various examples.

Referring now to FIG. 9, a block diagram of the operating system 40 of the storage compartment 10 is shown having control circuitry exemplarily illustrated as a controller 220 including a processor 224 and memory 228. The controller 220 may include other or additional analog and/or digital circuitry. The controller 220 may process input information from the memory 228 and generate an output to the charging assembly 80. As illustrated, the charging assembly 80 may correspond to an inductive charger having inductive coil(s) 232 configured to wirelessly transfer electrical energy for the purposes of charging one or more rechargeable batteries provided in the electronic device 18 positioned within the cavity 16 of the storage compartment 10.

The controller 220 may be configured to receive various inputs from the vehicle 12 via a communication bus 230 and each of the charging assembly 80 and the lighting assembly 30. For example, the inputs may include: 1) a signal indicative of a charging status of the device 18 (e.g. fully charged, partially charged, or low charging state/fully discharged), 2) information from a vehicle connectivity system via a vehicle communication bus 230 to at least one determination of a current charging status of the electronic device 18 detected via wireless technology or a Universal Serial Bus (USB) port of the vehicle connectivity connectively, 3) a feedback signal from the lighting assembly 30 identifying a disinfecting status, a disinfecting and cleaning status, and/or light source functionality. The information sent from the vehicle connectivity system may also include a request to the controller 220 to determine if the electronic device 18 is charging and a request for the charging status of the device 18 being charged. In some embodiments, the controller 220 may be configured to periodically broadcast a message indicating the charging status of the electronic device 18 to the vehicle connectivity system. In this way, the controller 220 may control the lighting assembly 30 to illuminate when the electronic device 18 is charging.

In some embodiments, the charging assembly 80 may comprise a charging sensor 234 configured to sense a presence or absence of receivers of the electronic device 18. The sensor 234 may be configured to detect a presence of the electronic device 18 in a transmitter area of the charging assembly 80. The sensor 234 may also measure the stored charging status of the battery within the electronic device 18. The electronic device 18 may be configured to transmit information indicating the stored charging status and the charging assembly 80 may be configured to receive a signal from the electronic device 18 indicative of a charging status of the electronic device 18. The transmitted information may indicate that the electronic device 18 is fully charged, partially charged, or at a low charging state/fully discharged. In some embodiments, an in-vehicle connectivity system may be enabled with a wireless communication protocol and may synchronize with the electronic device 18 enabled with the same protocol. Examples of wireless communication protocols that may be used by a chargeable device and compatible with the vehicle connectivity system include Bluetooth, infrared, 2-way UHF key fobs, and IEEE 802.11 technologies. In such cases, the charging status information of the electronic device 18 may be communicated directly to and from the electronic device 18 to a vehicle connectivity system without requiring sensing of the charging status of the electronic device 18 by the charging assembly 80. In various examples, the controller 220 may actuate the lighting assembly 30 when the electronic device 18 is charging.

The operating system 40 of the storage compartment 10 may further comprise at least one user input 238 in communication with the controller 220. For example, the actuator 74 may provide a user input 238. The user input 238 may be configured to initiate a disinfecting function of the lighting assembly 30. In response to receiving a signal from the user input 238, the controller 220 may activate the light source 34a of the lighting assembly 30. The light source 34a emits emitted light 36a within the UV light range which is configured to sterilize and sanitize an outer surface of the electronic device 18. Further, the emitted light 36a is configured to activate the first and second coatings 206, 208 to illuminate the cavity 16 of the storage compartment 10 and clean the outer surface of the electronic device 18 and the exposed surfaces of the storage compartment 10. The controller 220 may be configured to maintain the activation of the light source 34a to emit the emitted light 36a for a predetermined period of time that may correspond to a disinfection period. For example, the controller 220 may be configured to maintain the activation of the light source 34a for a first time frame for disinfecting. The first time frame may be about 1 minute to about 5 minutes or any time increment or range of time increments therebetween (e.g., 2 minutes). The controller 220 may also be configured to maintain the activation of the light source 34a for a second time frame for cleaning and disinfecting. The second time frame may be about 20 minutes to about 30 minutes, about 20 minutes to about 25 minutes, or any time increment or range of time increments therebetween. The emitted light 36a may also cause the photoluminescent structure 260 of the first coating 206 to become illuminated. In this way, the storage compartment 10 may be configured to identify and warn an occupant of the vehicle 12 that a disinfecting function is being processed in cavity 16.

When the controller 220 activates the light source 34a of the lighting assembly 30, the light source 34a may be illuminated for predetermined time increments including the first time frame for disinfecting and the second time frame for disinfecting and cleaning. When the light source 34a is illuminated for the second time frame, the light source 34a is deactivated at the end of the second time frame. The photoactive self-cleaning components of the second coating 208 remain active and continue to disinfect and clean for a third time frame. The third time frame may be about 15 to 25 minutes or any time increment or range of time increments therein (e.g., about 20 minutes).

In some embodiments, the operating system 40 of the storage compartment 10 may further comprise a door sensor 242 and a presence sensor 246 in communication with the controller 220. The door sensor 242 may comprise a switch, for example, a magnetic proximity switch, located proximate a closure surface corresponding to the door 26 and the body 14 of the storage compartment 10. The door sensor 242 may be configured to output a signal to the controller 220 in response to the door 26 being open or closed. In this way, the controller 220 may control the light source 34a such that the emitted light 36a within the UV light range is only output when the door 26 is closed.

The presence sensor 246 may be disposed in the body 14 of the storage compartment 10. For example, the presence sensor 246 may be positioned proximate the lower wall 22 of the body 14. In various examples, the presence sensor 246 may be one of two presence sensors 246 where one is positioned proximate the lower wall 22 and one is positioned within the shelf 28. The presence sensors 246 are operable to identify the presence of the electronic device 18 and/or any other object that may be positioned within the cavity 16. The presence sensor 246 may comprise a capacitive sensor, reflective sensor, light sensor, a weight sensor, or any other form of sensor operable to detect the presence of the electronic device 18 and/or any other object in the cavity 16. In response to the electronic device 18 and/or another object being located within the cavity 16, the presence sensor 246 may send a signal to the controller 220. In response to receiving the signal from the presence sensor 246, the controller 220 may activate the lighting assembly 30.

In various other examples, the user input 238 may include the actuator 74 positioned on or proximate the center stack portion 68 and/or center console 72. The actuator 74 may be a switch, button, knob, or any other actuator configured to provide input to the controller 220. The actuator 74 may have various states including, for example, "Off," "Disinfect," "Disinfect/Clean," "Illuminate," etc. The actuator 74 may be positioned proximate the display 70. The display 70 may be operably coupled with the controller 220 so that the controller 220 may actuate the display 70 to indicate the status of the storage compartment 10. The controller 220 may further actuate the display 70 to indicate completion of the selected cycle. Alternatively, the controller 220 may actuate one of the plurality of light sources 34a, 34b of the lighting assembly 30 to indicate that the function has been completed. For example, the lighting assembly 30 may include a light or photoluminescent portion configured to emit light to indicate a charging status, a disinfecting status, and/or a cleaning status of the storage compartment 10.

The use of the lighting assembly 30 with the first and second coatings 206, 208 provides a storage compartment 10 that can disinfect and/or clean objects positioned within the cavity 16 of the storage compartment 10. This allows a user to easily disinfect and/or clean objects using the emitted light 36a of the UV light source 34a of the lighting assembly 30. This also allows a user to disinfect and/or clean an electronic device 18 when the electronic device 18 is charging.

It will be understood by one having ordinary skill in the art that construction of the described invention and other components is not limited to any specific material. Other exemplary examples of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point, and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A storage compartment for a vehicle, comprising:
   a body defining a cavity configured to receive an electronic device, wherein the body includes an upper wall, a lower wall, and a rear wall;
   a door hingedly coupled with the body and configured to selectively seal the cavity;
   a shelf removably positioned within the cavity, the shelf configured to operably couple with the rear wall of the body;
   a lighting assembly positioned proximate the rear wall, wherein the lighting assembly includes a light guide and a light source positioned to direct emitted light through the light guide; and
   a charging assembly positioned proximate the lower wall of the body and configured to charge the electronic device.

2. The storage compartment of claim 1, wherein the light guide is integrally formed with the body.

3. The storage compartment of claim 1, wherein the shelf is formed as a secondary light guide and is configured to direct the emitted light from the light source.

4. The storage compartment of claim 1, further comprising:
   a first coating applied to one of the upper wall, the lower wall, and the rear wall, wherein the first coating is configured to absorb the emitted light from the light source and convert the emitted light to converted light to illuminate the cavity.

5. The storage compartment of claim 1, further comprising:
a door light guide positioned on an inner surface of the door, wherein the door light guide is configured to abut the light guide of the body.

6. The storage compartment of claim 1, further comprising:
a second coating applied to an inner surface of the light guide, wherein the second coating includes a photoactive self-cleaning material configured to be activated by the emitted light.

7. The storage compartment of claim 6, wherein the second coating is applied to a surface of the electronic device.

8. A storage compartment, comprising:
a body defining a cavity, wherein the body includes a rear wall defining an opening in communication with the cavity;
a shelf configured to be at least partially received by the opening of the rear wall;
a hinged member positioned to selectively conceal the opening of the rear wall; and
at least one light source positioned proximate the opening of the rear wall, wherein the shelf is configured to direct emitted light from the at least one light source into the cavity when the shelf is received by the opening of the rear wall, and further wherein the hinged member includes a protrusion having first and second sides, and the first and second sides are mirrored to direct emitted light from the at least one light source to one of a plurality of light guides when the hinged member is in a closed position.

9. The storage compartment of claim 8, further comprising:
a first coating applied to an inner surface of the body and is configured to absorb the emitted light from the at least one light source and convert the emitted light to converted light to illuminate the cavity.

10. The storage compartment of claim 8, wherein the at least one light source comprises a first light source positioned proximate a second light source, and further wherein one of the first and second light sources is an ultraviolet light-emitting diode.

11. The storage compartment of claim 8, further comprising:
a charging assembly positioned proximate a lower wall of the body.

12. The storage compartment of claim 8, wherein the plurality of light guides includes:
an upper light guide, a lower light guide, and a rear light guide, and further wherein the plurality of light guides are configured to direct the emitted light from the at least one light source into the cavity.

13. The storage compartment of claim 12, wherein the rear light guide has an upper portion and a lower portion positioned to frame the opening of the rear wall.

14. A storage compartment comprising:
a body defining a cavity, wherein the body includes an upper wall, a lower wall, and a rear wall;
a light source positioned proximate the rear wall, wherein the body is configured to direct emitted light from the light source into the cavity;
a first coating applied to an electronic device and an inner surface of the body, wherein the first coating includes a photoactive self-cleaning material activated by the emitted light from the light source; and
a charging assembly positioned proximate the lower wall of the body, the charging assembly configured to inductively charge the electronic device positioned within the cavity.

15. The storage compartment of claim 14, further comprising:
a second coating applied to an inner surface of the body, wherein the second coating includes a photoluminescent material configured to absorb the emitted light from the light source and convert the emitted light to converted light to illuminate the cavity.

16. The storage compartment of claim 14, further comprising:
a shelf removably positioned within the cavity and operably coupled with the body.

17. The storage compartment of claim 14, further comprising:
a controller configured to selectively actuate the charging assembly and the light source; and
an actuator configured to provide user input to the controller to activate at least one of the charging assembly and the light source.

18. The storage compartment of claim 17, wherein the actuator is integrally formed with a display.

* * * * *